United States Patent

Baumann et al.

[11] Patent Number: 5,426,192
[45] Date of Patent: Jun. 20, 1995

[54] CHROMOGENIC LACTAM COMPOUNDS, THEIR PREPARATION AND THEIR USE

[75] Inventors: Hans Baumann, Oberwil; Ian J. Fletcher, Magden, both of Switzerland

[73] Assignee: Ciba-Geigy Corporation, Ardsley, N.Y.

[21] Appl. No.: 224,384

[22] Filed: Apr. 7, 1994

Related U.S. Application Data

[62] Division of Ser. No. 755,717, Sep. 6, 1991, Pat. No. 5,329,006.

[30] Foreign Application Priority Data

Sep. 14, 1990 [CH] Switzerland .................. 2989/90
Jun. 13, 1991 [CH] Switzerland .................. 1759/91

[51] Int. Cl.$^6$ .................................. C07D 498/04
[52] U.S. Cl. .................................. 544/71; 544/89; 548/216; 548/217; 548/224
[58] Field of Search .............. 544/71, 89; 548/216, 548/217, 224

[56] References Cited

U.S. PATENT DOCUMENTS

| | | | |
|---|---|---|---|
| 3,336,306 | 8/1967 | Sulkowski | 544/89 |
| 3,408,350 | 10/1968 | Houlihan | 544/89 |
| 3,470,180 | 9/1969 | Houlihan | 544/252 |
| 3,491,111 | 1/1970 | Lin | 548/440 |
| 3,509,147 | 4/1970 | Houlihan | 544/246 |
| 3,591,599 | 7/1971 | Hoehn | 548/149 |
| 3,703,397 | 11/1972 | Lin | 503/220 |
| 3,936,564 | 2/1976 | Miyazawa | 428/307 |
| 4,032,690 | 6/1977 | Kohmura et al. | 503/217 |
| 4,058,529 | 11/1977 | Graf et al. | 544/252 |
| 4,062,866 | 12/1977 | Garner | 260/326 |
| 4,242,513 | 12/1980 | Hoover | 544/345 |
| 4,323,700 | 4/1982 | Kondo | 562/460 |
| 4,500,897 | 2/1985 | Matsuda | 503/217 |

FOREIGN PATENT DOCUMENTS

| | | |
|---|---|---|
| 51854 | 11/1965 | Germany . |
| 1670446 | 2/1971 | Germany . |
| 3008494 | 9/1980 | Germany . |

*Primary Examiner*—Emily Bernhardt
*Attorney, Agent, or Firm*—George R. Dohmann

[57] ABSTRACT

Chromogenic lactam compounds of the formula

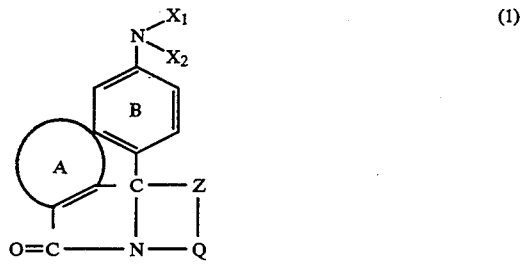

(1)

in which the ring A is an aromatic or heteroaromatic radical which has 6 ring atoms and may contain a fused aromatic ring, it being possible for both the ring A and the fused ring to be substituted;

the ring B is an unsubstituted or substituted benzene ring;

Z is

—NR,

O or S;

R is hydrogen; unsubstituted or substituted $C_1$–$C_{12}$alkyl, cycloalkyl having 5 to 10 carbon atoms; unsubstituted or substituted aryl or aralkyl; $C_1$–$C_{12}$acyl; N-(lower alkyl)carbamoyl; or N-arylcarbamoyl which is unsubstituted or substituted on the ring;

Q is $C_1$–$C_{12}$alkylene, aryl-$C_1$–$C_4$alkylene, 1,2-cycloalkylene, 1,2- or 1,8-arylene or aralkylene; and $X_1$ and $X_2$, independently of one another, are each hydrogen; unsubstituted or substituted alkyl having a maximum of 12 carbon atoms; acyl having 1 to 8 carbon atoms; cycloalkyl having 5 to 10 carbon atoms; or unsubstituted or ring-substituted aralkyl or aryl; or ($X_1$ and $X_2$), together with the common (Abstract continued on next page.)

nitrogen atom, are a five- or six-membered, preferably saturated, heterocyclic radical.

These lactam compounds are particularly suitable as colour formers in pressure- or heat-sensitive recording materials and give light-fast yellow, red, violet, blue, cyan or green shades.

8 Claims, No Drawings

CHROMOGENIC LACTAM COMPOUNDS, THEIR PREPARATION AND THEIR USE

This is a divisional of Ser. No. 755,717, filed Sep. 6, 1991, now U.S. Pat. No. 5,239,006.

The present invention relates to chromogenic lactam compounds, to a process for their preparation, and to their use in pressure- or heat-sensitive recording materials.

The lactam compounds according to the invention conform to the general formula

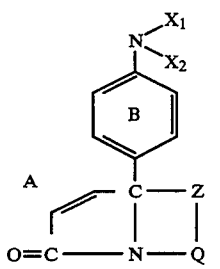

in which
the ring A is an aromatic or heteroaromatic radical which has 6 ring atoms and may contain a fused aromatic ring, it being possible for both the ring A and the fused ring to be substituted;
the ring B is a benzene ring which is unsubstituted or substituted by halogen, lower alkyl, $C_1$–$C_{12}$alkoxy, in particular lower alkoxy, benzyloxy, lower alkylcarbonylamino or mono- or di(lower alkyl)amino;
Z is

O or S;
R is hydrogen; $C_1$–$C_{12}$alkyl which is unsubstituted or substituted by halogen, hydroxy, cyano, benzoyl, $C_1$–$C_{12}$acyl, di(lower alkyl)amino or lower alkoxy; cycloalkyl having 5 to 10 carbon atoms; aryl or aralkyl, each of which is unsubstituted or ring-substituted by halogen, cyano, nitro, $C_1$–$C_4$haloalkyl, lower alkyl, lower alkoxy, lower alkoxycarbonyl or $C_1$–$C_{12}$acyl; $C_1$–$C_{12}$acyl; N-(lower alkyl)carbamoyl; or N-arylcarbamoyl which is unsubstituted or substituted on the ring;
Q is $C_1$–$C_{12}$alkylene, aryl-$C_1$–$C_4$alkylene, 1,2-cycloalkylene, 1,2-or 1,8-arylene or aralkylene; and
$X_1$ and $X_2$, independently of one another, are each hydrogen; alkyl having a maximum of 12 carbon atoms which is unsubstituted or substituted by halogen, hydroxy, cyano, tetrahydrofuryl or lower alkoxy; acyl having 1 to 8 carbon atoms; cycloalkyl having 5 to 10 carbon atoms; or aralkyl or aryl, each of which is unsubstituted or ring-substituted by halogen, cyano, nitro, trifluoromethyl, lower alkyl, lower alkoxy, lower alkoxycarbonyl, —NX'X'' or 4-X'X''N-phenylamino, in which X' and X'', independently of one another, are hydrogen, lower alkyl, cyclohexyl, benzyl or phenyl; or ($X_1$ and $X_2$), together with the common nitrogen atom, are a five- or six-membered, preferably saturated, heterocyclic radical.

A 6-membered aromatic ring A is preferably a benzene ring, which is unsubstituted or substituted by halogen, cyano, nitro, lower alkyl, lower alkoxy, lower alkylthio, lower alkylcarbonyl, lower alkoxycarbonyl, amino, lower alkylamino, di(lower alkyl)amino or lower alkylcarbonylamino. A 6-membered heterocyclic ring A is, in particular, a nitrogen-containing heterocyclic ring having an aromatic character, for example a pyridine or pyrazine ring. The ring A may also contain a fused aromatic ring, preferably a benzene ring, and is thus, for example, a naphthalene, quinoline or quinoxaline ring.

Preferred 6-membered aromatic or heterocyclic radicals A are 2,3-pyridino, 3,4-pyridino, 2,3-pyrazino, 2,3-quinoxalino, 1,2-naphthalino, 2,3-naphthalino or 1,2-benzo radicals, which are unsubstituted or substituted by halogen, such as a chlorine or bromine, nitro, lower alkyl, lower alkoxy, lower alkylthio or one of the substituted or unsubstituted amino groups as defined above, the 1,2-benzo radical, which is unsubstituted or substituted by chlorine atoms, lower alkoxy or preferably di(lower alkyl)amino, in particular by dimethylamino or diethylamino, being particularly preferred.

The ring B is advantageously a phenylene radical which is unsubstituted or substituted by halogen, lower alkyl, lower alkoxy, acetylamino or di(lower alkyl)amino. The ring B is particularly preferably a phenylene radical which is unsubstituted or substituted by lower alkoxy.

Z is advantageously —S—, —O— or

in which R' is hydrogen, lower alkyl, cyano(lower alkyl), lower alkylcarbonyl, such as acetyl, phenyl, benzyl, N-(lower alkyl)carbamoyl or N-phenylcarbamoyl (carbanilino) which is unsubstituted or substituted by halogen, nitro, trifluoromethyl, lower alkyl, lower alkoxy or lower alkoxycarbonyl. Z is preferably

phenyl or in particular —NH—.

An alkylene radical Q advantageously has 2 to 6 carbon atoms, preferably 2 or 3 carbon atoms, and may be straight-chain or branched. It is, for example, the —CH₂CH₂—,

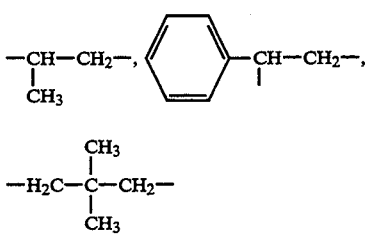

group and in particular the —CH₂CH₂CH₂—group. A branched alkylene radical Q additionally covers spirocyclically fused radicals, such as the

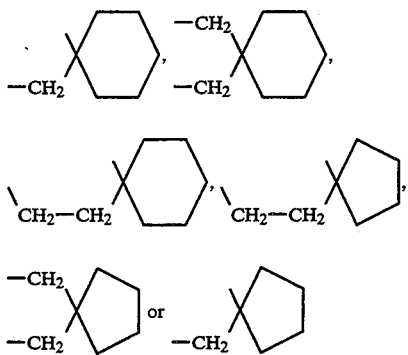

radical which may itself be unsubstituted or monosubstituted, disubstituted or trisubstituted by $C_1$–$C_4$alkyl.

Cycloalkylene Q is, in particular, 1,2-cyclohexylene or 1,2-cyclopentylene, preferably 1,2-cyclohexylene.

Arylene Q is preferably a 1,2-phenylene radical which is unsubstituted or substituted by halogen, methyl or methoxy. Arylene Q may advantageously be a 1,8-naphthylene radical or a diphenylene radical.

Q is preferably 1,2-phenylene, 1,2-cyclohexylene, 1,8-naphthalene, 1,2-ethylene (—$CH_2CH_2$—), neopentylene

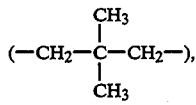

1,2-propylene

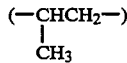

or in particular 1,3-propylene (—$CH_2$—$CH_2$—$CH_2$—).

Alkyl substituents R, $X_1$ and $X_2$ may be straight-chain or branched. Examples of such alkyl radicals are methyl, ethyl, n-propyl, isopropyl, n-butyl, 1-methylbutyl, sec-butyl, tert-butyl, amyl, isoamyl, n-hexyl, 2-ethylhexyl, n-heptyl, n-octyl, isooctyl, 1,1,3,3-tetramethylbutyl, n-nonyl, isononyl, 3-ethylheptyl, decyl or n-dodecyl.

Substituted alkyl radicals in R, $X_1$ and $X_2$ are, in particular, cyanoalkyl, haloalkyl, hydroxyalkyl or lower alkoxyalkyl, in each case preferably having a total of 2 to 8 carbon atoms, for example 2-cyanoethyl, 2-chloroethyl, 2-chloropropyl, 2-hydroxyethyl, 3-hydroxypropyl, 2-methoxyethyl, 2-ethoxyethyl, 2,3-dihydroxypropyl, 2-hydroxy-2-chloropropyl, 3-methoxypropyl, 4-methoxybutyl, trichloromethyl, trifluoromethyl, teuafluoroethyl, tetrachloroethyl and 4-propoxybutyl, and, in the case of $X_1$ and $X_2$, also tetrahydrofurfuryl.

Examples of cycloalkyl R, $X_1$ and $X_2$ are cyclopentyl, cycloheptyl and preferably cyclohexyl. Cycloalkyl radicals may contain one or more $C_1$–$C_4$alkyl radicals, preferably methyl groups, and have a total of 5 to 10 carbon atoms.

Aralkyl R, $X_1$ and $X_2$ may be phenethyl, phenylisopropyl or in particular benzyl. Aryl X and the substituent R are in particular naphthyl or primarily phenyl.

Examples of preferred substituents in the aralkyl or aryl group of the X radicals are halogen, cyano, methyl, trifluoromethyl, methoxy and carbomethoxy. Examples of preferred substituents in the aryl radical R are halogen, methyl and methoxy. Examples of aliphatic and aromatic radicals of this type are methylbenzyl, 2,4- and 2,5-dimethylbenzyl, chlorobenzyl, dichlorobenzyl, cyanobenzyl, tolyl, xylyl, chlorophenyl, methoxyphenyl, trifluoromethylphenyl, 2,6-dimethylphenyl and carbomethoxyphenyl.

If $X_1$ and $X_2$, together with the common nitrogen atom, are a heterocyclic radical, this is, for example, pyrrolidino, pipefidino, pipecolino, morpholino, thiomorpholino or piperazino, for example N-methylpiperazino or N-phenylpiperazino. Preferred saturated heterocyclic radicals for —$NX_1X_2$ are pyrrolidino, pipefidino and morpholino.

The substituents $X_1$ and $X_2$ are preferably cyclohexyl, tolyl, benzyl, phenyl, cyano(lower alkyl), for example 2-cyanoethyl, or primarily lower alkyl for example methyl, ethyl, n-propyl, isopropyl, n-butyl or isoamyl. —$NX_1X_2$ is preferably also pyrrolidino, N-(lower)alkyl-N-tetrahydrofurfurylamino, 4-di(lower alkyl)aminophenylamino or 4-(4'-phenylaminophenylamino)-phenylamino.

Lower alkyl, lower alkoxy and lower alkylthio are groups or moieties which have 1 to 6 carbon atoms, in particular 1 to 4 carbon atoms. Examples of groups of this type are methyl, ethyl, n-propyl, isopropyl, n-butyl, sec-butyl, amyl, isoamyl, hexyl, methoxy, ethoxy, isopropoxy, isobutoxy, tert-butoxy, amyloxy, methylthio, ethylthio, propylthio and butylthio.

Halogen is, for example, fluorine, bromine or preferably chlorine.

"Acyl" is in particular formyl, lower alkylcarbonyl, for example acetyl or propionyl, or benzoyl. Other possible acyl radicals are lower alkylsulfonyl, for example methylsulfonyl or ethylsulfonyl, lower alkoxysuffonyl, for example methoxysulfonyl or ethoxysulfonyl, phenylsulfonyl and phenoxysulfonyl. Benzoyl and phenylsulfonyl may be substituted by halogen, methyl, methoxy or ethoxy.

Particular mention should be made of the lactam compounds of the formula (1) in which A is a benzene ring which is unsubstituted or substituted by halogen, cyano, nitro, $C_1$–$C_4$alkyl, $C_1$–$C_4$alkoxy, $C_1$–$C_4$alkylthio, $C_1$–$C_4$alkylcarbonyl, $C_1C_4$alkoxycarbonyl, amino, $C_1$–$C_4$alkylamino, di-$C_1$–$C_4$alkylamino or $C_1$–$C_4$alkylcarbonylamino;

B is a benzene ring which is unsubstituted or substituted by halogen, $C_1$–$C_4$alkyl, $C_1$–$C_4$alkoxy, benzyloxy, $C_1$–$C_4$alkylcarbonylamino or mono- or di-$C_1$–$C_4$alkylamino;

Z is

O or S;

R is hydrogen; $C_1$–$C_4$alkyl which is unsubstituted or substituted by halogen, cyano, benzoyl, $C_1$–$C_4$alkylcarbonyl, phenoxysulfonyl, phenylsulfonyl, $C_1$–$C_4$-alkylsulfonyl, di-$C_1$–$C_4$alkylamino or $C_1$–$C_4$alkoxy; phenyl or benzyl, each of which is unsubstituted or ring-substituted by halogen, nitro or trifluoromethyl; $C_1$–$C_4$alkylcarbonyl; $C_1$–$C_4$alkyl-$SO_2$;$C_1$–$C_4$alkoxy-$SO_2$; N-$C_1$–$C_4$alkylcarbamoyl; or N-phenylcaxbamoyl which is unsubstituted or ring-substituted by $C_1$–$C_4$alkyl, halogen, $C_1$–$C_4$alkoxy, $C_1$–$C_4$haloalkyl, nitro, or cyano;

Q is $C_2$-$C_3$alkylene which is unsubstituted, monosubstituted or disubstituted by $C_1$-$C_4$alkyl, phenyl or $C_5$-$C_6$spiroalkyl; 1,2-cyclohexylene; 1,2-cyclopentylene; 1,2-phenylene; 1,8-naphthylene; 1,2-naphthylene; 1,3-naphthylene; or

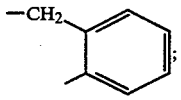

and $X_1$ and $X_2$, independently of one another, are each hydrogen; $C_1$-$C_4$alkyl which is unsubstituted or substituted by $C_1$-$C_4$alkoxy, hydroxy or cyano; $C_1C_4$alkylcarbonyl; or ($X_1$ and $X_2$), together with the common nitrogen atom, are a five- or six-membered, saturated heterocyclic radical.

Particularly important lactam compounds conform to the formula

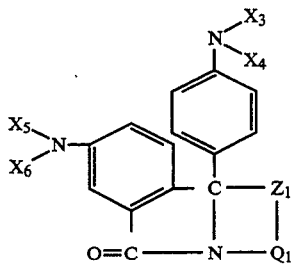

in which $X_3$ and $X_4$ and $X_5$ and $X_6$ are identical or different lower alkyl or phenyl radicals; or $X_3$ and $X_4$, together with the nitrogen atom to which they are bonded, are pyrrolidine;

$Q_1$ is $C_2$-$C_3$alkylene, 1,2-cyclohexylene, 1,2-phenylene or 1,8-naphthylene;

$Z_1$ is —O—, —S— or

and $R_1$ is hydrogen, phenyl, benzyl, $C_1$-$C_4$alkyl, cyano-$C_1$-$C_4$alkyl, $C_1$-$C_4$alkylcarbonyl, N-$C_1$-$C_4$alkylcarbamoyl, or N-phenylcarbamoyl which is unsubstituted or substituted by halogen, nitro, trifluoromethyl, lower alkyl or lower alkoxy.

Preferred lactam compounds of the formula (2) are the compounds in which the X radicals are identical and are lower alkyl, such as n-butyl, ethyl or, in particular, methyl. $Q_1$ is preferably $C_2$-$C_3$alkylene or 1,2-phenylene. $Z_1$ is preferably

and $R_1$ is, in particular, hydrogen, phenyl, lower alkyl or cyano(lower alkyl).

Of particular interest are lactam compounds of the formula

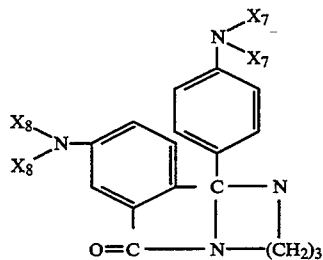

in which $X_7$ and $X_8$, independently of one another, are $C_1$-$C_4$alkyl and in particular methyl, and $R_2$ is hydrogen, phenyl, $C_1$-$C_4$alkyl or cyano(lower alkyl).

The lactam compounds of the formulae (1) to (3) according to the invention are novel compounds and can be prepared by methods which are known per se.

The lactam compounds according to the invention are advantageously prepared by reacting a keto acid of the formula

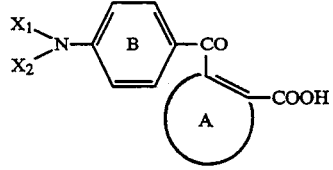

with a bifunctional amino compound of the formula $H_2N$-Q-Z-H (5)

in which, in the formulae (4) and (5), A, B, $X_1$, $X_2$, Q and Z are as defined above.

The reaction is expediently carried out under reflux in an organic solvent which does not participate in the condensation.

Suitable organic solvents which form the reaction medium are cycloaliphatic or preferably aromatic hydrocarbons, for example cyclohexane, benzene, toluene or xylene; chlorinated hydrocarbons, for example ethylene chloride, tetrachloroethylene or chlorobenzenes, for example chlorobenzene, chlorotoluene or dichlorobenzene; cyclic ethers, for example dioxane or tetrahydrofuran; dimethyl sulfoxide or nitriles of aliphatic monocarboxylic acids, for example acetonitrile, propionitrile or butyronitrile. Mixtures of said solvents can also be used. Preferred solvents are chlorobenzene, chlorotoluene and in particular toluene.

The end product is isolated in a generally known manner by separating off the resultant water phase and removing the solvent or by treatment with suitable organic solvents, for example methanol, isopropanol or petroleum ether.

The starring materials of the formula (4) are described, for example, in DE-A-1 795 737, DE-A-2 709 580, GB-A-1 443 617 and U.S. Pat. No. 4,062,866.

The bifunctional compounds of the formula (5) can be employed as diamines, amino alcohols or mercaptoamines, depending on the meaning of Z.

Suitable amino compounds of the formula (5) for the reaction with the keto acids of the formula (4) are 1,2-ethylenediamine, 1,2-propylenediamine, 1,3- propylenediamine, 1,2-phenylenediamine, 1,2-xylenediamine, 1,8-naphthalinediamine, 2,2′-diaminodiphenyl, 1,2-cyclohexylenediamine, 2-mercaptoethylamine, 2-hydroxyethylamine, 2-mercaptopropylamine, 3-mercaptopropylamine, 3-hydroxypropylamine, 1-amino- 2-hydroxycyclohexane, 2-aminophenol, 2-aminothiophenol, 2-aminobenzyl alcohol, 2-amino- 1-butanol, 1-amino- 2-butanol, 2-amino-1-phenylethanol, 2-amino- 1-phenyl-1-propanol, 2,2-dimethyl-1,3-propylenediamine, 3-amino- 2,2-dimethyl-1-propanol, 2-amino- 1,3-propanediol, N-methylethylenediamine, N-methyl- 1,3-propylenediamine, N-n-butyl- 1,3-propylenediamine, N-tert-butyl- 1,3-propylenediamine, N-2-cyanoethylethylenediamine, N-2′-cyanoethyl-1,3-propylenediamine, N-cyanoisopropylethylenediamine, N-cyanoisopropyl 1,3-propylenediamine, N-phenylethylenediamine, N-phenyl- 1,3-propylenediamine, N-benzylethylenediamine, N-benzyl- 1,3-propylenediamine, N-cyclohexyl- 1,3-propylenediamine, 1-aminomethylcyclohexanol, 2-(2′-aminoethyl)phenol, N′-[3-aminopropyl]-N,N-dimethylhydrazine, 2-(2′-hydroxyethyl)aniline, o-aminomethylphenol and 1-amino-methyl-1-cyclohexanol.

Compounds of the formula (1) in which Z is

and R is acyl, N-(lower alkyl)-carbamoyl or substituted or unsubstituted N-phenylcarbamoyl can also be prepared by reacting a lactam compound of the formula (1) in which Z is —NH— in a conventional manner with a reactive functional derivative of a carboxylic acid or of a sulfonic acid, in particular a halide or anhydride, for example acetic anhydride, acetyl chloride, acetyl bromide, benzoyl chloride or benzenesulfonyl chloride, or alternatively with an isocyanate, for example a lower alkyl isocyanate, phenyl isocyanate, halophenyl isocyanate or lower alkylphenyl isocyanate.

The lactam compounds of the formulae (1) to (3) are normally colourless or at most pale coloured. Bringing these colour formers into contact with a preferably acidic developer, for example an electron acceptor, gives, depending on the meaning of Z and on the developer used, intense yellow, red, violet, cyan, blue or green shades which are fast to sublimation and light. The lactams of the formulae (1) to (3) are also very valuable when mixed with one or more other known colour formers, for example 3,3-(bisaminophenyl)phthalides, such as CVL, 3-indolyl-3-aminophenylaza- or -diazaphthalides, (3,3-bisindolyl)phthalides, 3-aminofluorans, 2,6-diaminofluorans, 2,6-diamino-3-methylfluorans, 3,6-bisalkoxyfluorans, 3,6-bisdiarylaminofluorans, leukoauramines, spiropyrans, spirodipyrans, chromenopyrazoles, chromenoindoles, phenoxazines, phenothiazines, quinazolines, rhodamine lactams, carbazolylmethanes or other triarylmethane-leuko dyes, for giving navy blue, grey or black dyeings.

The lactam compounds of the formulae (1) to (3) have excellent colour intensity and light fastness both on activated clays and on phenolic substrates. They are particularly suitable as colour formers for use in a heat-sensitive or in particular pressure-sensitive recording material, which may be both a copying material and a registering material. They are distinguished by the fact that they are pH-stable and readily soluble in capsule oils. After exposure in a CB sheet, they show little decrease in colour strength (CB deactivation).

A pressure-sensitive material comprises, for example, at least one pair of sheets which contain at least one colour former of the formulae (1) to (3) dissolved in an organic solvent and an electron acceptor as developer.

Typical examples of developers of this type are active clay substances, such as attapulgite, acid clay, bentonite, montmorillonite, activated clay, for example acid-activated bentonite or montmorillonite, furthermore zeolite, halloysite, silicon dioxide, aluminium oxide, aluminium sulfate, aluminium phosphate, zinc chloride, zinc nitrate, zirconium dioxide, activated kaolin or any desired clay. The developers may also be acidic organic compounds, for example unsubstituted or ring-substituted phenols, resorcinols, salicylic acids, for example 3,5-bis(α,α-dimethylbenzyl)salicylic acid or 3,5-bis(α-methylbenzyl)-salicylic acid or salicylic acid esters and metal salts thereof, for example zinc salts, and an acidic, polymeric material, for example a phenolic polymer, an alkylphenol acetylene resin, a maleic acid-colophony resin or a partially or fully hydrolysed polymer of maleic anhydride with styrene, ethylene or vinyl methyl ether, or carboxymethylene. It is also possible to use mixtures of said monomeric and polymeric compounds. Particularly preferred developers are acid-activated bentonite, zinc salicylates, for example zinc 3,5-bis-α-methylbenzylsalicylate, or the products of the condensation of p-substituted phenols with formaldehyde. The latter may also be zinc-modified. The zinc salicylates are described, for example, in EP-A-181 283 and DE-A-2 242 250.

The developers may additionally also be employed in a mixture with pigments which are unreactive or only slightly reactive per se or with further assistants, such as silica gel or UV absorbers, for example 2-(2′-hydroxyphenyl)benzotriazoles or 2-hydroxyphenyl-1,2,3-triazines. Examples of pigments of this type are: talc, titanium dioxide, aluminium oxide, aluminium hydroxide, zinc oxide, chalk, clays, such as kaolin, and organic pigments, for example urea-formaldehyde condensates (BET surface area 2–75 m$^2$/g) or melamine-formaldehyde condensation products.

The colour former produces a coloured mark at the points where it comes into contact with the electron acceptor. In order to prevent premature activation of the colour formers present in the pressure-sensitive recording material, they are generally separated from the electron acceptor. This may expediently be achieved by incorporating the colour formers into foam-, sponge- or honeycomb-like structures. The colour formers are preferably enclosed in microcapsules, which generally burst under pressure.

When the capsules burst under pressure, for example by means of a pencil, the colour former solution is transferred onto an adjacent sheet which is coated with an electron acceptor, producing a coloured point. The colour results from the dye formed by this process, which absorbs in the visible region of the electromagnetic spectrum.

The colour formers are preferably encapsulated in the form of solutions in organic solvents. Examples of suitable solvents are preferably nonvolatile solvents, for example halogenated paraffin, benzene or diphenyl, such as chloroparaffin, trichlorobenzene, monochlorodiphenyl, dichlorodiphenyl or trichlorodiphenyl, esters, for example tricresyl phosphate, di-n-butyl phthalate, diocytyl phthalate, trichloroethyl phosphate, aromatic ethers, such as benzyl phenyl ether, hydrocarbon oils, such as paraffin or kerosene, aromatic hydrocarbons, for example isopropyl- isobutyl-, sec-butyl- or tert-butyl-alkylated derivatives of diphenyl, naphthalene or terphenyl, ctibenzyltoluene, partially hydrogenated terphenyl, mono- to tetra-$C_1$-$C_3$alkylated diphenylalkanes, dodecylbenzene, benzylated xylenes, phenylxylylethane or other chlofinated or hydrogenated, condensed, aromatic hydrocarbons. Mixtures of various solvents, in particular mixtures of paraffin oils or kerosene and diisopropylnaphthalene or partially hydrogenated terphenyl, are frequently employed in order to achieve optimum solubility for the colour formation, rapid and intense coloration and a viscosity which is favourable for microencapsulation. In the case of encapsulation, the lactams according to the invention are distinguished by the fact that they are readily soluble and pH-stable, for example in a pH range of from 4 to 10.

The capsule walls may be formed uniformly around the droplets of the colour former solution by coacervation forces, the encapsulation material being described, for example, in U.S. Pat. No. 2,800,457. The capsules may preferably also be formed by polycondensation from an aminoplastics or modified aminoplastics, as described in British patents 989 264, 1 156 725, 1 301 052, 4 100 103 and 1 355 124. Also suitable are microcapsules formed by interface polymerisation, for example capsules made from polyester, polycarbonate, polysulfonamide, polysulfonate, but in particular from polyamide, polyurea or polyurethane.

The microcapsules containing colour formers of the formulae (1) to (3) can be used to produce pressure-sensitive copying materials of a very wide variety of known types. The various systems essentially differ from one another through the arrangement of the capsules, the colour reactants and the base material.

In a preferred arrangement, the encapsulated colour former is in the form of a coating on the reverse of a transfer sheet and the electron acceptor (colour developer) is in the form of a coating on the front of a receiving sheet. In another arrangement of the constituents, the developer and the microcapsules containing the colour former are in or on the same sheet in the form of one or more individual coatings or the developer is incorporated into the base material.

The capsules are preferably fixed on the base material by means of a suitable binder. Since paper is the preferred base material, this binder is principally a paper size, such as gum arabic, polyvinyl alcohol, hydroxymethylcellulose, casein, methylcellulose, dextrin, starch, starch derivatives or polymer latexes. The latter are, for example, butadiene-styrene copolymers or acrylic homopolymers or copolymers.

The papers used are not only normal papers comprising cellulose fibres, but also papers in which some or all of the cellulose fibres have been replaced by fibres made from synthetic polymers. The coating base may also be a plastic film.

The copying material also preferably contains a capsule-free coating containing the colour former and a colour-developing coating which contains, as colour developer, at least inorganic metal salt of a polyvalent metal, in particular a halide or nitrate, for example zinc chloride, tin chloride, zinc nitrate or a mixture thereof.

The compounds of the formulae (1) to (3) may also be used as colour formers in a thermoreactive recording material. This generally contains at least one coating base, one or more colour formers, and an electron acceptor and possibly also a binder and/or wax. If desired, activators or sensitizers, for example benzyldiphenyl, may also be present in the recording material.

Thermoreactive recording systems include, for example, heat-sensitive recording and copying materials and papers. These systems are used, for example, for recording information, for example in electronic calculators, telex machines, fax machines or in recording instruments and measuring instruments, for example electrocardiographs. The image generation (marking) can also be carried out manually using a heated stylus. Another way of generating markings by means of heat is to use laser beams.

The thermoreactive recording material may be constructed in such a manner that the colour former is dissolved or dispersed in a binder layer and the developer is dissolved or dispersed in the binder in a second layer. Another possibility is for both the colour former and the developer to be dispersed in one layer. The layer or layers are softened in specific areas by means of heat, and the desired colour then develops immediately in the warmed areas.

Suitable developers are the same electron acceptors as are used in pressure-sensitive papers. Examples of developers are the abovementioned clay minerals and phenolic resins, or alternatively phenolic compounds, such as, for example, those described in German patent 1 251 348, for example 4-tert-butylphenol, 4-phenylphenol, methylenebis(p-phenylphenol), 4-hydroxydiphenyl ether, $\alpha$-naphthol, $\beta$-naphthol, methyl or benzyl 4-hydroxybenzoate, 4-hydroxydiphenyl sulfone, 4'-hydroxy-4-methyldiphenyl sulfone, 4'-hydroxy-4-isopropoxydiphenyl sulfone, 4,4'-cyclohexylidenediphenol, 4,4'-isopropylidenediphenol, 4,4'-isopropylidenebis-(2-methylphenol), an antipyrine complex of zinc thiocyanate, a pyridine complex of zinc thiocyanate, 4,4-bis(4-hydroxyphenyl)valeric acid, hydroquinone, pyrogallol, phloroglucinol, p-, m-, and o-hydroxybenzoic acid, hydroxyphthalic acid, gallic acid, 1-hydroxy-2-naphthoic acid, and boric acid or organic, preferably aliphatic, dicarboxylic acids, for example tartaric acid, oxalic acid, maleic acid, citric acid, citraconic acid or succinic acid.

In the production of the thermoreactive recording material, fusible, film-forming binders are preferably used. These binders are normally water-soluble, while the lactams and the developer are insoluble or virtually insoluble in water. The binder should be capable of dispersing and fixing the colour former and the developer at room temperature.

On exposure to heat, the binder softens or melts, so that the colour former comes into contact with the developer and a colour is able to form. Examples of water-soluble or at least water-swellable binders are hydrophilic polymers, such as polyvinyl alcohol, polyacrylic acid, hydroxyethylcellulose, methylcellulose, carboxymethylcellulose, polyacrylamide, polyvinylpyrrolidone, gelatin, starch or etherified maize starch.

If the colour former and the developer are in two separate layers, water-insoluble binders, ie binders which are soluble in nonpolar or only slightly polar solvents, for example natural rubber, synthetic rubber, chlofinated rubber, alkyd resins, polystyrene, styrene-butadiene copolymers, polymethyl acrylates, ethylcellulose, nitrocellulose and polyvinylcarbazole, can be used. However, the preferred arrangement is that in which the colour former and the developer are present in one layer in a water-soluble binder.

In order to ensure the stability of the heat-sensitive recording material or the image density of the developed image, the material may be provided with an additional protective coating. Such protective coatings generally comprise water-soluble and/or water-insoluble resins, which are conventional polymer materials or aqueous emulsions of these polymer materials.

The thermoreactive layers and resin layers may contain additional additives. In order to improve the whiteness, to facilitate printing of the papers and to prevent bonding to the heated stylus, these layers may contain, for example, talc, titanium dioxide, zinc oxide, aluminium hydroxide, calcium carbonate (for example chalk), clays or organic pigments, for example urea-formaldehyde polymers. In order to ensure that the colour is only formed within a limited temperature range, substances such as urea, thiourea, diphenylthiourea, acetamide, acetanilide, benzenesulfanilide, stearamide, bisstearoylethylenectiamide, phthalic anhydride, metal stearates, for example zinc stearate, phthalonitrile, dimethyl terephthalate, dibenzyl terephthalate or other appropriate fusible products which induce simultaneous melting of the colour former and of the developer, can be added. Thermographic recording materials preferably contain waxes, for example carnauba wax, montan wax, paraffin wax, polyethylene wax, condensates of higher fatty amides and formaldehydes and condensates of higher fatty acids and ethylenediamine.

A further use of the compounds of the formulae (1) to (3) is in the production of a colour image by means of photocurable microcapsules, as described, for example, in DE-A-3 247 488.

In the examples below, percentages are by weight, unless stated otherwise.

Example 1

15.6 g of 2-(4'-dimethylaminobenzoyl)-5-dimethylaminobenzoic acid are slurried in 100 ml of toluene, and 7.4 g of 1,3-propylenediamine are added. The reaction mixture is refluxed until the water phase produced remains constant. After addition of petroleum ether, the product crystallises on being left to stand. Separation and drying give 17 g of a lactam compound of the formula

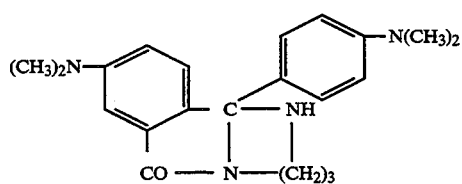

(11)

having a melting point of 191°–193° C.

Example 2

If Example 1 is repeated using 32 g of 2-(4'-dimethylaminobenzoyl)-5-dimethylaminobenzoic acid and 12 g of ethylenediamine instead of 1,3-propylenediamine, 30.6 g of a lactam compound of the formula

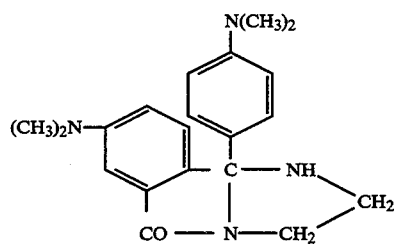

(12)

having a melting point (m.p.) of 178°–179° C. are obtained.

Example 3

If Example 1 is repeated with the 1,3-propylenediamine replaced by 8.8 g of 3-methylaminopropylamine in 130 ml of toluene and 0.1 g of p-toluenesulfonic acid, a lactam compound of the formula

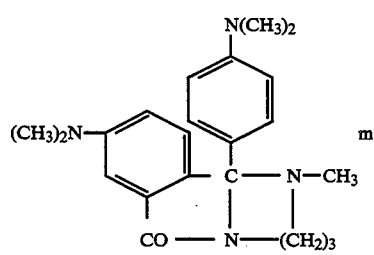

(13)

m.p. 145–148° C.

is obtained.

Example 4

If Example 1 is repeated with the 1,3-propylenediamine replaced by 6.1 g of ethanolamine in 100 ml of toluene and the process is otherwise carried out as described in the example, 6 g of a lactam compound of the formula

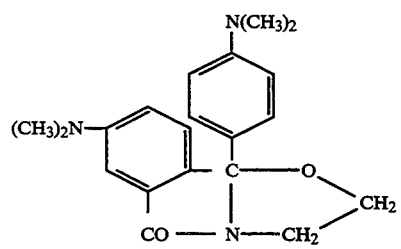

(14)

are obtained after chromatography.

Example 5

If Example 1 is repeated with the 1,3-propylenediamine replaced by 4.62 g of cysteamine and the procedure is otherwise as described in the example, the lactam compound of the formula

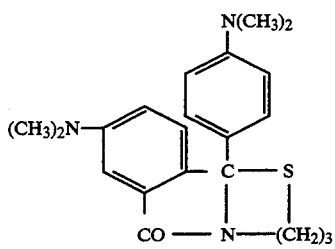

is obtained as a yellowish oil.

Example 6

If Example 1 is repeated using 2.4 g of phenylenediamine instead of the 1,3-propylenediamine and the procedure is otherwise as described in the example, the lactam compound of the formula

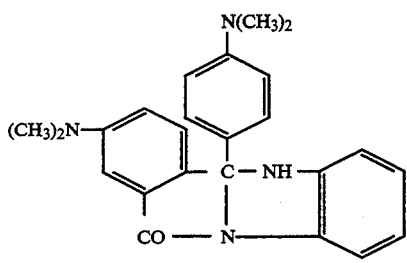

having a melting point of 266°–268° C. is obtained.

Example 7

If Example 1 is repeated with the 1,3-propylenediamine replaced by 7.5 g of 3-amino- 1-propanol with addition of 0.1 g of p-toluenesulfonic acid and the procedure is otherwise as described in the example, 12.1 g of a lactam compound of the formula

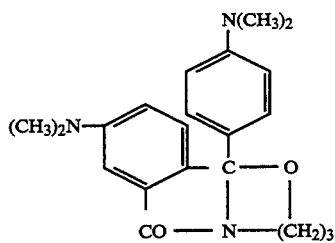

having a melting point of 143°–146° C. are obtained.

Example 8

13.3 g of 2-(4'-dimethylaminobenzoyl)benzoic acid are slurried in 150 ml of toluene, and 6 g of ethylenediamine are added. The reaction mixture is refluxed until the water phase produced remains constant. Petroleum ether is added, and the product crystallises on being left to stand. Separation and drying give 12.2 g of a lactam compound of the formula

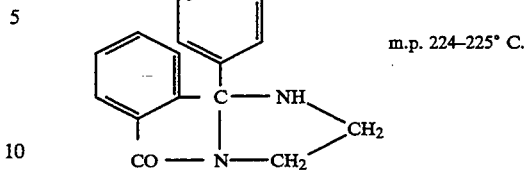

m.p. 224–225° C.

Example 9

If Example 8 is repeated with the starring materials indicated therein replaced by 7.5 g of 2-(4'-di-n-butylamino-2'-ethoxybenzoyl)benzoic acid and 2.3 g of ethylenediamine, 7.32 g of a yellow oil of a lactam compound of the formula

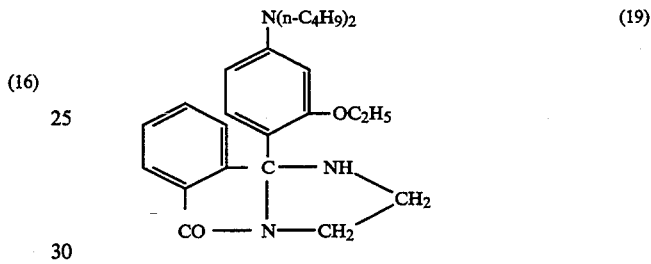

are obtained.

Example 10

If Example 8 is repeated with the ethylenediamine replaced by 3.66 g of ethanolamine, a lactam compound of the formula

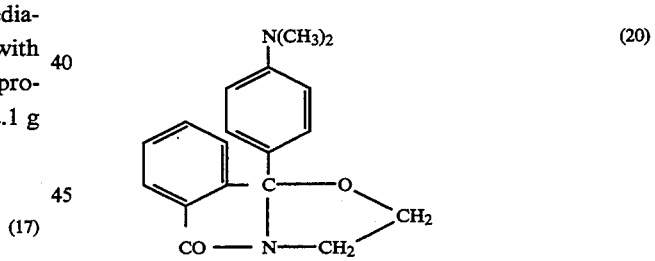

having a melting point of 89°–90° C. is obtained.

Example 11

If Example 8 is repeated with the ethylenediamine replaced by 4.62 g of cysteamine and the procedure is otherwise as described in the example, 9.19 g of a lactam compound of the formula

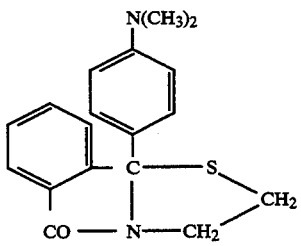

are obtained after chromatography.

Example 12

4.4 g of 2-(4'-dimethylaminobenzoyl)-5-dimethylaminobenzoic acid are slurried in 150 ml of toluene and allowed to react with 2.2 g of 2,2-dimethyl-1,3-propylenediamine with addition of 0.3 g of p-toluenesulfonic acid. 2.9 g of a lactam compound of the formula

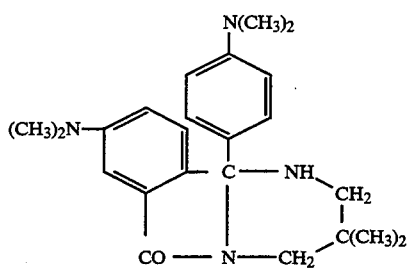
(22)

having a melting point of 221°–223° C. (decomp.) are obtained.

Example 13

8.9 g of 2-(4'-diethylaminobenzoyl)-5-dimethylaminobenzoic acid are slurried in 200 ml of toluene and allowed to react with 3.8 g of 1,3-propylendiamine as described in Example 1. 6.9 g of a lactam compound of the formula

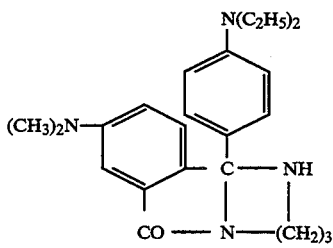
(23)

having a melting point of 161°–163° C. are obtained.

Example 14

4.4 g of 2-(4'-dimethylaminobenzoyl)-5-dimethylaminobenzoic acid are reacted as described in Example 1 with 2.9 g of (±)-2-amino-1-phenylethanol. 4.32 g of a 2:1 diastereomer mixture of the lactam compound of the formula

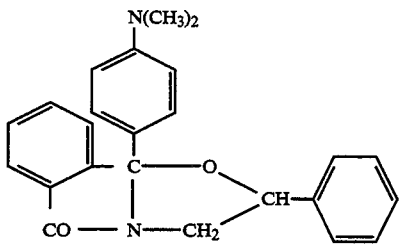
(24)

having a melting point of 233°–235° C. are obtained.

Example 15

If Example 14 is repeated with the (±)-2-amino-1-phenylethanol replaced by 1.6 g of 1-amino-2-propanol and the procedure is otherwise as described in the example, 4.9 g of the 2:1 diastereomer mixture of the formula

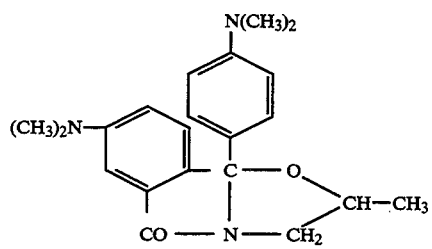
(25)

having a melting point of 62°–65° C. are obtained.

Example 16

10.3 g of the lactam compound of the formula (18) prepared as described in Example 8, 35 ml of acetic anhydride and 3 drops of boron trifluoride etherate are heated to the boil. Cooling gives 6.7 g of a lactam compound of the formula

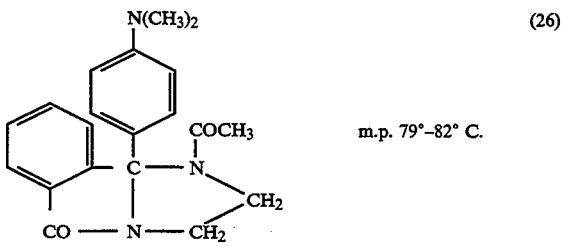
(26) m.p. 79°–82° C.

Example 17

If Example 16 is repeated with the lactam compound of the formula (18) replaced by the lactam compound of the formula (11), 1.6 g of the lactam compound of the formula

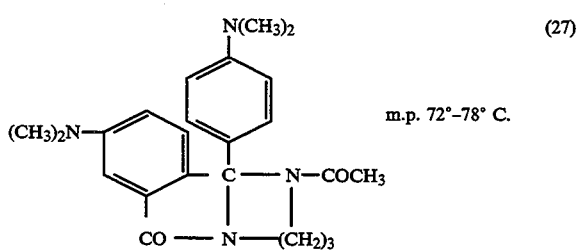
(27) m.p. 72°–78° C.

are obtained.

Example 18

1.8 g of phenyl isocyanate in 3.5 ml of toluene are added slowly to 5.25 g of the lactam compound of the formula (11) prepared as described in Example 1, in 40 ml of toluene. The reaction mixture is first stirred at room temperature and then warmed to 60° C. The toluene solution is then evaporated to dryness, and the residue is taken up in acetone and treated with a little n-heptane. 5.45 g of a lactam compound of the formula

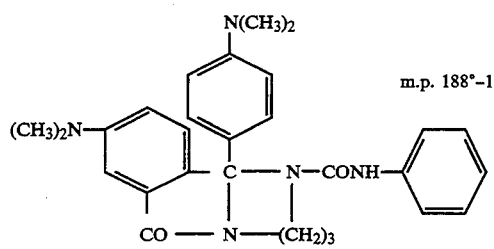

are obtained.

Example 19

4.4 g of 2-(4'-dimethylaminobenzoyl)-5-dimethylaminobenzoic acid and 1.9 g of R(—)-2-aminobutanol are reacted analogously to Example 14, giving 4.4 g of the diastereomer mixture of the formula

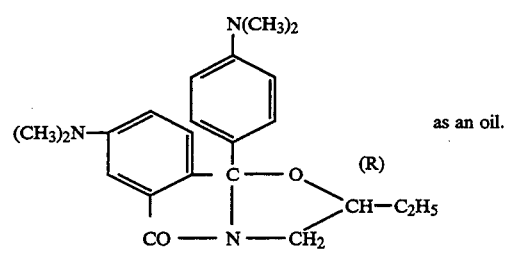

Example 20

4.4 g of 2-(4'-dimethylaminobenzoyl)-5-dimethylaminobenzoic acid and 2.6 g of o-aminomethylphenol are reacted analogously to Example 14 giving 5.1 g of the compound of the formula

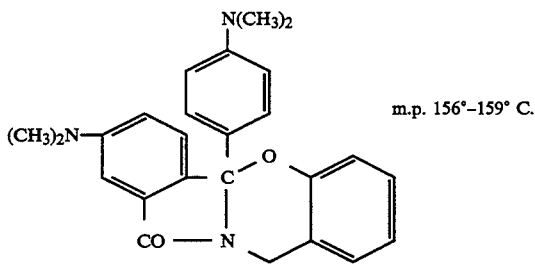

Example 21

1.6 g of 2-(4'-dimethylaminobenzoyl)-5-dimethylaminobenzoic acid and 1.0 g of 1-aminomethyl-1-cyclohexanol hydrochloride in 75 ml of toluene are reacted analogously to Example 12 giving 1.9 g of the compound of the formula

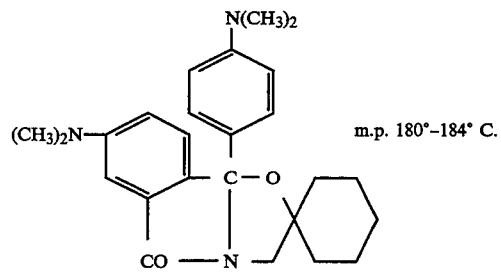

Example 22

9.4 g of 2-(4'-dimethylaminobenzoyl)-5-dimethylaminobenzoic acid and 5.0 g of o-aminophenylethanol in 150 ml of toluene are reacted analogously to Example 12, giving 2.3 g of the compound of the formula

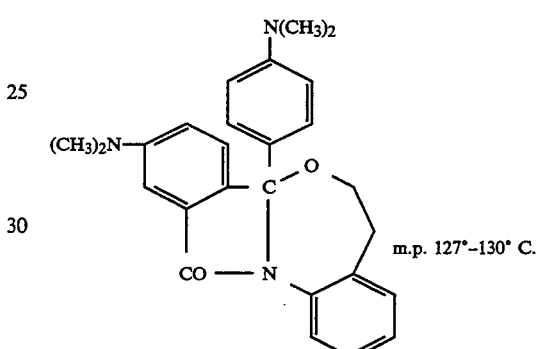

Example 23

5.11 g of 2-(2'-ethoxy-4-pyrrolidinobenzoyl)benzoic acid and 1.8 g of 3-amino-1-propanol in 100 ml of toluene are heated on a water separator until water is no longer produced. The mixture is cooled and evaporated, giving a colourless product, which is filtered off and washed with ethanol. 2.5 g of the compound of the formula

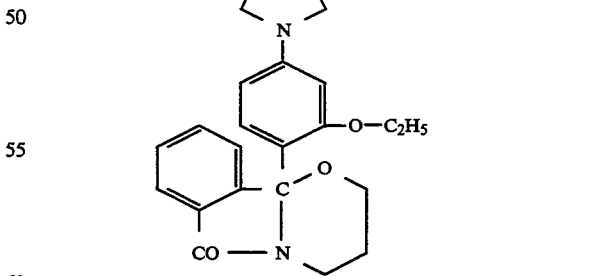

having a melting point of 188°–190° C. are isolated.

Example 25

11.2 g of 2-(N-methyl-N-phenylaminobenzoyl)benzoic acid and 3.7 g of diaminopropane are reacted analogously to Example 1, giving 7.0 g of the compound of the formula

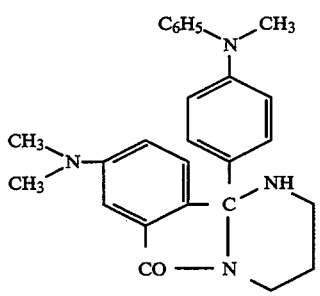

having a melting point of 202°–206° C.

Examples 26–32

Lactam compounds of the formula (35)

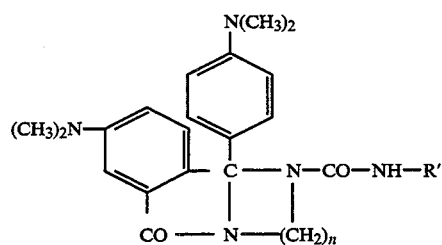

are prepared as described in Example 18 using the appropriate isocyanate instead of phenyl isocyanate.

TABLE 1

| Ex. | R' | n | m.p. |
|---|---|---|---|
| 26 | ―⟨C₆H₄⟩―CH₃ | 3 | 215–217° C. |
| 27 | ―⟨C₆H₄⟩―CF₃ | 3 | 221° C. |
| 28 | ―⟨C₆H₄⟩―CH(CH₃)₂ | 3 | 204–205° C. |
| 29 | ―⟨C₆H₄⟩―NO₂ | 3 | 212° C. |
| 30 | ―⟨C₆H₄⟩―CH₃ | 2 | 196–198° C. |
| 31 | ―⟨C₆H₄⟩―CF₃ | 2 | 174–177° C. |
| 32 | ―⟨C₆H₄⟩―CH(CH₃)₂ | 2 | 176–178° C. |

Examples 33–47

Lactam compounds of the formula (36)

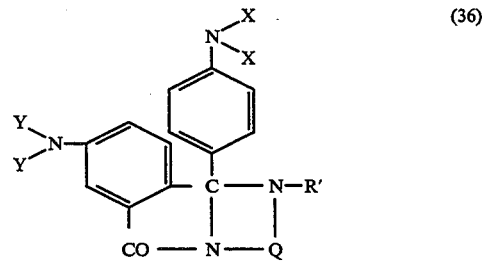

are prepared as described in Example 1 using the appropriate N-substituted diamine instead of 1,3-propylenediamine.

TABLE 2

| Ex. | Q | R' | X | Y | m.p. |
|---|---|---|---|---|---|
| 33 | ―(CH₂)₃― | -n-C₄H₉ | CH₃ | CH₃ | 124–125° C. |
| 34 | ―(CH₂)₃― | ―C₂H₄CN | CH₃ | CH₃ | 161–163° C. |
| 35 | ―(CH₂)₃― | ―CH₂―⟨C₆H₅⟩ | CH₃ | CH₃ | 102–103° C. |
| 36 | ―(CH₂)₃― | ―⟨C₆H₅⟩ | CH₃ | CH₃ | 104–106° C. |
| 37 | ―(CH₂)₃― | ―CHCH₂CN<br>    \|<br>    CH₃ | CH₃ | CH₃ | 103–108° C. |
| 38 | ―CH₂CH₂― | ―CH₃ | CH₃ | CH₃ | 131–133° C. |
| 39 | ―CH₂CH₂― | ―CH₂CH₂CN | CH₃ | CH₃ | 178–181° C. |

TABLE 2-continued

| Ex. | Q | R' | X | Y | m.p. |
|---|---|---|---|---|---|
| 40 | —CH$_2$CH$_2$— | —CHCH$_2$CN<br>\|<br>CH$_3$ | CH$_3$ | CH$_3$ | 194–196° C. |
| 41 | —CH$_2$CH$_2$— | 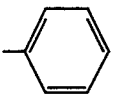 | CH$_3$ | CH$_3$ | 238–240° C. |
| 42 | —(CH$_2$)$_3$— | —N(CH$_3$)$_2$ | CH$_3$ | CH$_3$ | oil |
| 43 | —(CH$_2$)$_3$— | —CH$_3$ | n-C$_4$H$_9$ | CH$_3$ | 129–131° C. |
| 44 | —(CH$_2$)$_3$— | —CH$_2$CH$_2$N(CH$_3$)$_2$ | CH$_3$ | CH$_3$ | oil |
| 45 | —(CH$_2$)$_3$— | —(CH$_2$)$_2$—OCH$_2$CH$_3$ | CH$_3$ | CH$_3$ | oil |
| 46 | —(CH$_2$)$_3$— | —CH$_2$CH$_2$SO$_2$C$_6$H$_5$ | CH$_3$ | CH$_3$ | oil |
| 47 | —CH$_2$CH$_2$— | —CH$_2$CH$_2$SO$_3$C$_6$H$_5$ | CH$_3$ | CH$_3$ | oil |

Example 48

Production of a pressure-sensitive copying paper.

A solution of 3 g of the lactam compound of the formula (11) (Example 1) in 80 g of diisopropylnaphthalene and 17 g of kerosene is microencapsulated by coacervation in a known manner using gelatin and carboxymethylcellulose, mixed with starch solution and coated onto a sheet of paper. A second sheet of paper is coated on the front with activated clay as colour developer. The first sheet, containing the colour former, and the paper coated with colour developer are placed one on top of the other with the coatings adjacent. Pressure is exerted on the first sheet by handwriting or typewriting, and an intense green copy with excellent light fastness properties develops on the sheet coated with the developer.

Example 33

1 g of the lactam compound of the formula (11) as described in Example 1 is dissolved in 17 g of toluene. 12 g of polyvinyl acetate, 8 g of calcium carbonate and 2 g of titanium dioxide are added to this solution with stirring. The resultant suspension is diluted with toluene in the weight ratio 1:1 and coated onto a sheet of paper using a 10 μm doctor blade. A second sheet of paper whose underside has been coated at an application weight of 3 g/m$^2$ with a mixture comprising 1 part of an amide wax, 1 part of a stearin wax and 1 part of zinc chloride is placed on this sheet of paper. Pressure is exerted on the upper sheet by handwriting or typewriting, and an intense, light-fast green colour develops on the sheet coated with the colour former.

What is claimed is:

1. A lactam compound of the formula

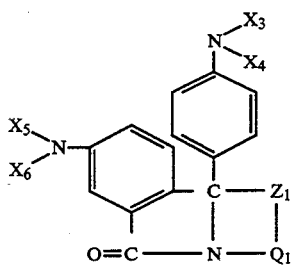

in which

X$_3$ and X$_4$ are identical lower alkyl or phenyl radicals; or

X$_3$ and X$_4$ together with the nitrogen atom to which they are bonded are a pyrrolidine ring;

X$_5$ and X$_6$ are hydrogen, lower alkyl or phenyl radicals;

Q$_1$ is C$_2$–C$_3$alkylene which is unsubstituted, monosubstituted or disubstituted by C$_1$–C$_4$alkyl, phenyl or C$_5$–C$_6$spiroalkyl; and Z$_1$ is O.

2. A lactam of claim 1 wherein X$_5$ and X$_6$ are identical lower alkyl or phenyl radicals.

3. A lactam of claim 2 wherein X$_3$, X$_4$, X$_5$ and X$_6$ are each lower alkyl.

4. A lactam of claim 3 wherein X$_3$, X$_4$, X$_5$ and X$_6$ are each methyl.

5. A lactam of claim 1 wherein Q$_1$ is unsubstituted, monosubstituted or disubstituted C$_3$alkylene.

6. A lactam of claim 5 wherein X$_5$ and X$_6$ are identical lower alkyl or phenyl radicals.

7. A lactam of claim 6 wherein X$_3$, X$_4$, X$_5$ and X$_6$ are each lower alkyl.

8. A lactam of claim 7 wherein X$_3$, X$_4$, X$_5$ and X$_6$ are each methyl.

* * * * *